United States Patent [19]

Paré

[11] Patent Number: 5,675,909
[45] Date of Patent: Oct. 14, 1997

[54] MICROWAVE-ASSISTED SEPARATIONS USING VOLATILES

[75] Inventor: J.R. Jocelyn Paré, Gloucester, Canada

[73] Assignee: Her Majesty the Queen in right of Canada, as represented by the Minister of Environment, Ottawa, Canada

[21] Appl. No.: 721,952

[22] Filed: Sep. 27, 1996

Related U.S. Application Data

[60] Division of Ser. No. 653,553, May 24, 1996, and a continuation-in-part of Ser. No. 327,638, Oct. 24, 1994, Pat. No. 5,519,947, which is a continuation-in-part of Ser. No. 12,475, Feb. 2, 1993, Pat. No. 5,377,426.

[30] Foreign Application Priority Data

Feb. 10, 1992 [CA] Canada ................... 2060931

[51] Int. Cl.⁶ .................................................. F26B 3/34
[52] U.S. Cl. .................. 34/265; 24/305; 24/381; 24/417; 24/480; 436/177; 436/181
[58] Field of Search ................. 34/265, 305, 381, 34/402, 405, 417, 467, 480, 497, 516, 517; 436/177, 181; 219/690

[56] References Cited

U.S. PATENT DOCUMENTS

| 2,064,422 | 12/1936 | Fenske et al. | 196/13 |
|---|---|---|---|
| 2,505,139 | 4/1950 | Pascal | 23/210 |
| 2,925,328 | 2/1960 | Romagnan | 23/267 |
| 3,706,631 | 12/1972 | Falk | 195/1.8 |
| 4,168,418 | 9/1979 | Bird | 219/10.55 |
| 4,221,580 | 9/1980 | Hardwick et al. | 252/301.1 |
| 4,294,858 | 10/1981 | Moule | 426/241 |
| 4,400,398 | 8/1983 | Coenen et al. | 426/429 |
| 4,464,402 | 8/1984 | Gannon | 426/242 |
| 4,480,993 | 11/1984 | Guiriec | 432/266 |
| 4,554,132 | 11/1985 | Collins | 422/68 |
| 4,673,560 | 6/1987 | Masse et al. | 423/532 |
| 4,694,133 | 9/1987 | LeViet | 219/10.55 |
| 4,808,782 | 2/1989 | Nakagawa et al. | 219/10.55 |
| 4,837,142 | 6/1989 | Charm | 422/21 |
| 4,898,673 | 2/1990 | Rice et al. | 210/634 |

(List continued on next page.)

FOREIGN PATENT DOCUMENTS

| 4790285 | 10/1988 | Australia | C11B 9/02 |
|---|---|---|---|
| 2026103 | 3/1992 | Canada | 204/109 |
| 1209675 | 10/1970 | United Kingdom | C11B 1/04 |
| 2004197 | 3/1979 | United Kingdom | . |

OTHER PUBLICATIONS

Flavour & Fragrance Journal, vol. 4, 43–44 (1984) Microwave Oven Extraction of an Essential Oil, A.A. Craveiro, et al., University Federal do Ceara, Ceara, Brazil.

Microwave-Extraction–a new method superseding Soxhtet extraction–Katalin Ganzler et al. Central Research Institute for Chemistry, pp. 274–276.

Journal of Chromatography–371(1986) 299–306–Microwave Extraction–A Novel Sample Preparation Method For Chromatography–Katalin Ganzler et al.

Les Aléas de la Fraîcheur sous Sachet–Feb. 26, 1990–Revue de l'Industrie Agro-Alimentare–Bimensuel.

*Primary Examiner*—John M. Sollecito
*Assistant Examiner*—Steve Gravini
*Attorney, Agent, or Firm*—Paul Sharpe

[57] ABSTRACT

The generation of volatiles from liquid or solid materials is enhanced and accelerated by exposure to microwave radiation. Normally the energy transfer is effected preferentially toward the liquid or solid materials over the generated gaseous volatiles. Sufficient energy is provided at a selected rate that enhances the generation of volatiles to effect removal as vapor or to produce a pressurized vapor phase. Flow-through separations from a matrix having a microwave-absorbing liquid component are conducted by exposing to microwave radiation to vaporize this component and processing the vapor either by flowing through a selective permeable membrane, or by enclosing the vapor and matrix in a confined space and flowing matrix through a selected separation medium, and recovering residual matrix. These separations are particularly useful in analysis contexts.

11 Claims, 4 Drawing Sheets

U.S. PATENT DOCUMENTS

| | | | |
|---|---|---|---|
| 4,929,462 | 5/1990 | Moorman et al. | 426/478 |
| 5,002,784 | 3/1991 | Paré et al. | 426/241 |
| 5,003,143 | 3/1991 | Marks et al. | 219/10.55 |
| 5,024,952 | 6/1991 | Alsop | 436/177 |
| 5,026,565 | 6/1991 | McLachlan et al. | 426/241 |
| 5,290,403 | 3/1994 | Sääsk | 202/182 |
| 5,377,426 | 1/1995 | Paré | 34/259 |
| 5,492,838 | 2/1996 | Pawliszyn | 436/178 |
| 5,519,947 | 5/1996 | Paré | 34/263 |
| 5,581,903 | 12/1996 | Botich | 34/265 X |
| 5,605,564 | 2/1997 | Collins | 34/417 X |

# MICROWAVE-ASSISTED SEPARATIONS USING VOLATILES

This application is a division of application No. 08/653,553, filed May 4, 1996, (now pending). This is a continuation-in-part application of U.S. Ser. No. 08/327,638 filed Oct. 24, 1994, (now U.S. Pat. No. 5,519,947 issued May 28, 1996), which is in turn a continuation-in-part of application No. 08/012,475, filed Feb. 2, 1993, now U.S. Pat. No. 5,377,426 issued Jan. 3, 1995.

FIELD OF THE INVENTION

This invention relates to a method of generating volatile compounds from a variety of matrices containing volatilizable compounds therein. More particularly, this invention relates to a method and apparatus for the generation of volatile materials which can be achieved in a greatly reduced time frame as compared with conventional volatile expression or generation techniques. The volatiles may be separated or used to enhance other separations, e.g. in flow-through processes.

BACKGROUND OF THE INVENTION

Grains containing fats and oils have been dried by microwave heating followed by steps to remove husks and to extract oils, as indicated in U.S. Pat. No. 4,464,402, Aug. 7, 1984 (Gannon). The use of microwave energy to heat an extractant medium has also been investigated by Ganzler & Salgo, 1987, *Z. Lebensm Unters Forsch* 184: 274–276. In the latter type of application, most of the microwave energy is absorbed by the extractant subsequently resulting in the heating of the extractant; accordingly, very little energy reaches the inner parts of the material to be extracted.

Plant material has been exposed to microwave energy in an air stream to produce headspace-like samples of volatile material as documented by Craveiro et al., 1989, *Flavour and Fragrance Journal* 4: 43–44. No documentation has been compiled in terms of the ability to generate volatiles in a dynamic mode, such as those produced by purge and trap methods, and further no novel apparatus therefor has been set forth.

Canadian Patent No. 987,993 issued to Heitkamp et al., describes a microwave-induced migration of flavours and aromas to the surface of materials, such as tobacco or tea, in the presence of moisture and optionally, a solvent. In U.S. Pat. No. 5,002,784, Paré et al., teach that biological materials containing microwave absorbing substances, which are subjected to microwave radiation while in contact with an extractant microwave transparent or partial transparent, results in differential heating of the material to be extracted. The latter effects a disruption of the inner glandular and vascular systems of the material and causes a very rapid selective extraction of a variety of natural products.

The prior art fails to recognize the usefulness of microwave generation of volatile components from a matrix containing the same, followed by processing of the residual matrix. Further, the prior art is deficient in terms of any teaching pertaining to the disruption of the equilibrium between the liquid or solidphase containing the volatilizable components and the gaseous phase containing volatilized components or any apparatus capable of effecting the latter.

SUMMARY OF THE INVENTION

The present invention is directed to solving these deficiencies and further provides an apparatus which may be associated with other analytical devices, e.g. supercritical fluid and gas or liquid chromatography instruments, during the process of generating the volatilizable components.

The need for a general method to generate volatiles both, in a static, and in a dynamic mode, and an apparatus therefor which can be used for a variety of sources or origins, is well recognized. The fragrance, food and environmental industries, in particular, require methods and apparatus that are versatile, relatively inexpensive to operate and that do not involve intricate operations that increase the risks of sample loss and sample contamination.

The extraction industry, the petroleum industry, the health and safety industries associated with emergencies such as those related to chemical spills, in particular, require methods that are versatile with respect to the substance(s), to be selected, relatively inexpensive, simple and safe to operate to minimize the hazards associated with the generation and subsequent handling of substances under that particular state.

In accordance with aspects of the present invention, protocols for the generation of volatiles from any liquid or solid matrix can be performed (more easily and with greater efficiency and expediency; such advantages additionally permit less error and less contamination possibilities) when a microwave applicator is used to enhance the volatility of substances that are present in the matrices and, optionally, to disrupt the equilibrium between the liquid or solid phase of the matrix and the resultant gaseous phase from the volatilization of the substances. This procedure may be performed in a closed container so as to bring the chemical composition of the gaseous phase similar or identical to that present originally in the liquid or solid phase, or optionally, to bring one or all of the substances to a supercritical state.

One object of the present invention is to provide a process for generating volatiles or supercritical fluid material from any liquid or solid matrix by the steps comprising: (a) providing volatiles in a subdivided form within a liquid or solid matrix and comprising one or more substances contained in a closed container or the like; (b) exposing the subdivided material, while within the solid or liquid matrix, to microwave radiation and disrupting the equilibrium between the solid or liquid phase and the gaseous phase in favour of the gaseous phase without physically removing the volatiles, until substantial volatilization of the material has occurred; (c) subsequently separating the thus created gaseous phase from the solid or liquid phase while still in the same container, or in another container connected thereto, and optionally; (d) recovering the gaseous phase from the same container or another container connected thereto; or optionally (e) exposing the subdivided material to microwave radiation until sufficient energy has been imparted to bring the material to its supercritical state.

In the above process, and in some cases, the volatiles can be used in applications where their isolation is not required.

Further, where it is desirable to obtain volatiles in the gaseous phase in a relative concentration so as to be similar or substantially identical to that originally present in the solid or liquid phase, the microwave irradiation in step (b) is maintained for a sufficiently long period to effect a disruption of the equilibrium normally present between the gaseous, and the solid or liquid phase, so as to impart energy preferentially to the liquid or solid phase thus resulting in the generation of volatiles in the gaseous phase in the desired proportions.

Preferably, Where the desired substances are readily amenable to established analytical protocols, for example, a chromatographic separation coupled to an appropriate detector, the gaseous phase arising from the microwave treatment is delivered directly into the selected analytical device(s) using the apparatus described herein.

Still further, where the desired components are in trace amounts with respect to other substances of relatively different volatility, the invention may be employed in such a manner as to effect the selective and successive volatilization of the various substances. It will be apparent to those skilled in the art that the order in which the components will be volatilized will be determined by the characteristics of the components, namely, the vapor pressure and the dielectric constant.

The microwave dose should be chosen to maximize the volatilization of the desired components, or the conversion to the supercritical state of the desired substance, in a minimal amount of time, without affecting the nature of the components and by selecting appropriate operating parameters based on the nature of the components. The absolute value of the dielectric constant, the heat capacity, the enthalpy of formation, the ionization energy being some of the essential characteristics for this process.

Yet another object of this invention is to provide a method for expressing volatilizable components from a liquid or solid matrix containing the volatilizable components, comprising: providing a matrix having volatilizable components dispersed therein; exposing the matrix to microwave energy to effect volatilization of at least one of the volatilizable components; and separating at least one volatilized component from the matrix.

In addition to the foregoing, there is a need for a method of enhancing the volatility of substances present in a matrix having volatilizable components which permits disruption of the equilibrium between the liquid or solid phase of the matrix and the gaseous phase that results from the volatilization, to thereby establish a product which has a chemical composition, in terms of its gaseous phase, which is substantially similar or identical to that present in the original matrix.

A further embodiment of the present invention satiates the aforementioned need and provides., as a further object of the invention, a method of selectively separating volatilizable materials from a liquid or solid matrix containing the volatilizable materials comprising: providing a matrix selected from a solid or liquid, the matrix having volatilizable materials dispersed therein; enclosing the matrix within a container, the container having a selectively permeable membrane associated therewith, the membrane adapted to selectively pass at least one of the volatilizable materials when volatilized; exposing the matrix to microwave energy to effect volatilization of at least one of the volatilizable components in the matrix; and passing at least one volatilized component through the membrane.

As volatility is a physical characteristic specific to a given compound, selectivity of expression for volatilizable compounds contained within a given matrix for selective removal, is desirable. Such removal reduces the likelihood of expressed compounds containing contaminants and results in a generally more efficient expression protocol.

The present invention addresses the favourable technique outlined above and another object of the present invention, is to provide a method of sequentially separating volatilizable components from a matrix containing the components each having a different volatility, the improvement comprising the steps of: providing a matrix having volatilizable materials dispersed therein; enclosing the matrix within a container, the container having a selectively permeable membrane associated therewith, the membrane adapted to selectively pass through at least one of the volatilizable materials when volatilized; exposing, in a first exposure step, the matrix to a microwave applicator at a first energy intensity to effect volatilization of at least one of the volatilizable components; removing at least a first volatilized component; exposing, in a second exposure step, the matrix to the microwave applicator at a second energy intensity to effect volatilization of at least one of the volatilizable components remaining in the matrix.

The invention includes a method of improving flow-through separations from a matrix having a microwave-absorbing liquid component, the steps including exposing a flow of the matrix to microwave radiation treatment to vaporize microwave-absorbing liquid;

processing the vapor in one of the following two ways:
i) flowing the vapor through a permeable membrane selective therefor and removing the vapor; and
ii) enclosing the vapor and matrix in a confined space in contact with a separation medium and flowing treated matrix through this separation medium to separate a component; and
recovering the residual matrix.

Of particular interest are continuous flow embodiments where the microwave-induced vaporization is continuous or continual.

Another aspect of the invention covers a method of rendering a solid or liquid matrix containing a preferentially microwave-absorbing liquid and a component to be analyzed or processed, more suitable for such analysis or processing, the method including exposing the matrix to microwave energy to vaporize at least one microwave-absorbing liquid;

passing a vaporized liquid through a selective permeable membrane to separate a vaporized component before the matrix is heated significantly;

recovering the residual matrix and any residual vapor; and
passing the residual matrix and any residual vapor to means selected from analysis means and processing means. One preferred example is the vaporization of water and its separation through a selective water-permeable membrane. Another is where two volatiles are generated concurrently with only one being separated through a selective permeable membrane. In preparing mixtures for liquid chromatography it is desired to remove water (or any polar liquid that boils at a temperature below water), and according to this example water is removed as vapor through a water-selective membrane. Another example is where a moist solid matrix is treated to remove water as vapor, and the dry matrix is further processed e.g. by eluting an analyte into a non-aqueous solvent, or into an elevated temperature gas flow.

A further aspect involves a method of increasing the rate of filtration of a liquid matrix through a filter able to separate a relatively non-microwave-absorbing component of the matrix, the matrix including a microwave-absorbing liquid, this method involving exposing the liquid matrix to microwave radiation to vaporize the microwave-absorbing liquid in a confined space upstream of the filter thereby generating a pressure against the filter surface; and maintaining the pressure by continued microwave radiation exposure while passing the matrix through the filter to generate a filtrate.

In one preferred aspect a water-based matrix is treated, with only part of the water being vaporized. The amount of microwave energy used can be adjusted to control the pressure to a desired range.

The invention further includes an apparatus for the removal of a microwave-absorbing liquid from a matrix containing the liquid in a flow-through manner, having an elongated vessel having an inlet and an outlet and adapted to contain a flow of the matrix;

a microwave inlet adapted to feed microwave radiation into the vessel near the inlet end;

a selective permeable membrane in a wall portion of the vessel downstream of the microwave inlet;

a vented or vacuum-subjected enclosure surrounding the membrane; and means to feed matrix into the inlet of the vessel.

The invention includes also an apparatus for separating a separable component from a liquid matrix having a microwave-absorbing liquid component, including a vessel having an inlet and an outlet with an outlet zone just upstream of the outlet;

a substantially non-deformable separation medium extending across the vessel just upstream of the outlet zone;

the vessel inlet being positioned to introduce the liquid matrix upstream of the separation medium;

the vessel providing for a liquid zone to be spread over the separation medium and a vapor zone to be spread over the liquid zone; and a microwave inlet positioned to direct microwave radiation into the liquid zone.

Having thus generally described the invention, reference will now be made to the accompanying drawings illustrating preferred embodiments.

DETAILED DESCRIPTION OF THE PREFERRED EMBODIMENTS

Figure 1:
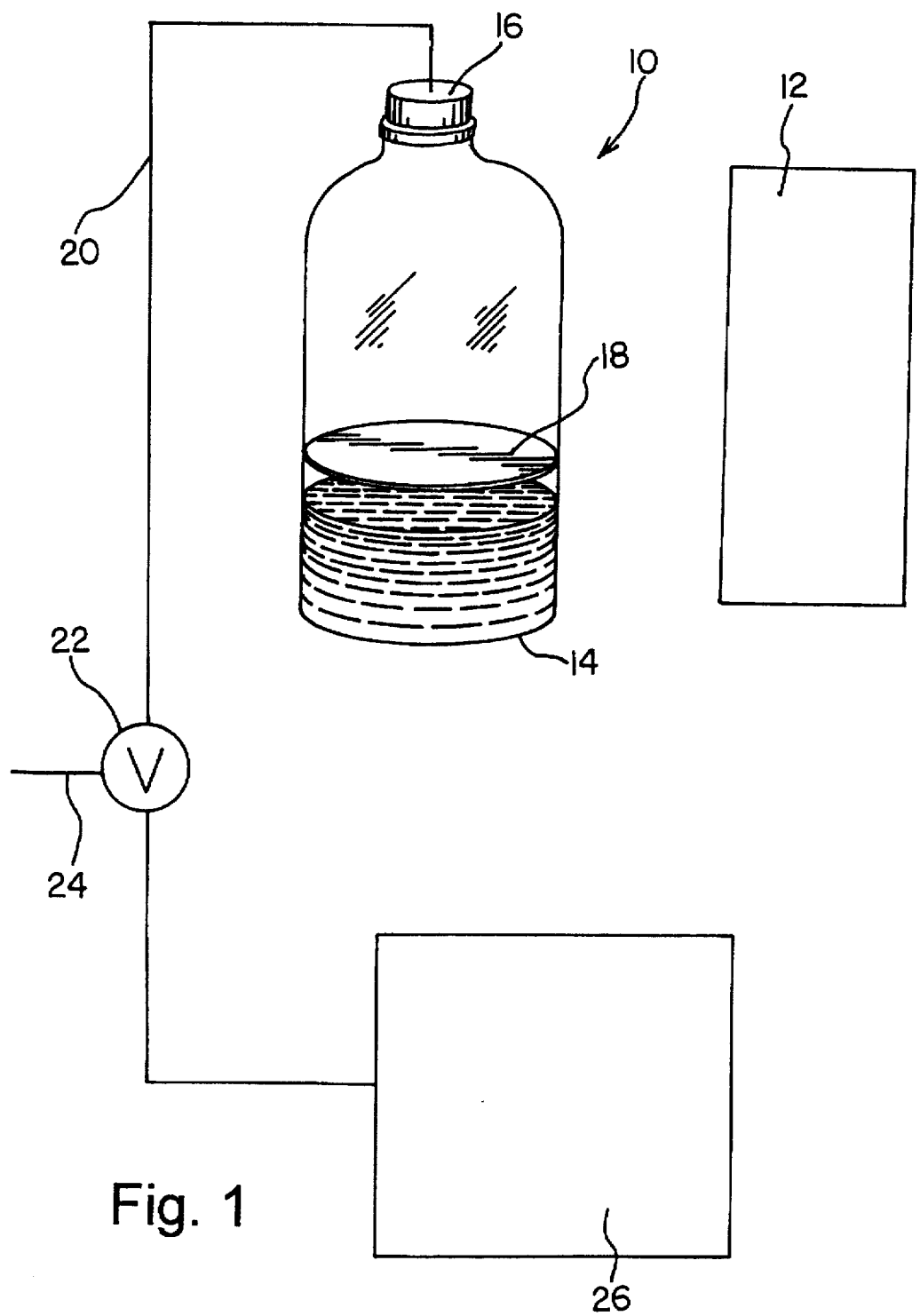
FIG. 1 is a schematic of an apparatus to effect the separation of volatiles, and subsequent direct transfer of the volatiles into another discrete unit.

The mechanism of action of this volatile generation process has been investigated using a variety of matrices and conventional sorbents to trap the volatiles evolved. The volatiles were monitored in comparison to those obtained when conventional methods were applied to identical matrices.

These investigations led to the conclusions that the microwave-assisted process proceeds generally as set forth herein. The microwave rays travel freely through the container (selected from those materials partially transparent to microwave rays) and reach the matrix. The matrix is made up of more than one component, each of which possesses characteristic physical properties and, more particularly, dielectric constant and a characteristic vapor pressure. The relative ability exhibited by each of the components to absorb the microwave rays is dependent upon the absolute value of their respective dielectric constant. Generally, components, such as water, possess a large dielectric constant at room temperature and therefore absorb to a great extent the microwave rays. The absorption of the microwave rays subsequently results in the heating of such compounds.

It is possible to control the power of the applied microwave rays so as to ensure an overall heating rate that is constant for each component as the heat so-generated is diffused passively to all of the components throughout the matrix. The rate of volatilization of each component, within a given matrix, is dependent upon the respective vapor pressure thereof. Water, for example, has a lower vapor pressure than benzene, hence benzene will volatilize more rapidly, at a given temperature, than water, thus a net effect of volatilizing the benzene preferentially to the water.

Under conventional steady state heating such as that applied by other technologies, such as conventional headspace analysis, the relative concentration of the volatiles in the gaseous phase is at substantial equilibrium with that in the solid or liquid phase of the matrix and is dependent upon the partial vapor pressure of each component; accordingly, the relative concentration of a given component in the gas phase is not equal to that while in the solid or liquid phase. This poses difficulties during analysis and specifically upon an attempt to quantify a material dispersed in a matrix.

Furthermore, the absolute value of the dielectric constant of a given substance decreases when the substance reaches the gas phase, e.g. liquid water has a dielectric constant of about 80 at 293° K. while steam, at 373° K., has a value of about 1. Hence, almost all of the applied microwave energy is used to selectively heat the liquid or solid phase of the matrix. Moreover, the capacity of a substance to absorb energy while resisting a temperature increase is dependent upon the heat capacity of the substance. As an example, the temperature of 1 gram of water is elevated by only 1° K. when the same absorbs 1 calorie of energy at 293° K.

Having regard to the above, the present invention makes it possible to effectively apply a controlled amount of microwave energy that will selectively heat the liquid phase at a temperature such that the volatiles are maintained in the gaseous phase without volatilizing the non-volatiles. This permits the application of more energy into the matrix to disrupt the phase equilibrium that normally prevails between the gaseous phase and the solid or liquid phase of the matrix as the energy is preferentially absorbed by the liquid, or solid, fraction of the system over the gaseous fraction. Under such conditions, it is possible to generate volatiles into the gas phase so that their relative gaseous concentration is substantially equal to that which they had in the liquid or solid state. This aspect of the invention relates to the generation of volatiles in a purge and trap fashion.

In a further embodiment of the present invention, the gaseous phase can be separated from the liquid or solid phase of the matrix, while enhancing the rate of volatilization, by incorporating the use of an appropriate selectively or semi-permeable membrane that allows the flow of gaseous materials in one direction (away from the matrix) while preventing the flow of liquid or solid materials. The functional use of such membranes will be well-known to those skilled in the art and there are several known types which are used for given bands of selectivity. Preferably, but not exclusively, a membrane that does not allow the passage of water, whether in a liquid or a gaseous state, is appropriate for direct transfer of the volatiles onto an inlet port of an analytical device such as a gas chromatograph. FIG. 1, as described hereinafter, depicts a typical apparatus for this purpose.

In another configuration of this invention, a protocol can be designed to generate supercritical fluids from a variety of materials, water being of particular interest. The dielectric constant of water is about 80 at 293° K. At its boiling point, namely 373° K., water has a dielectric constant of about 55 whereas steam has a dielectric constant of about 1. Thus, it is possible to heat all of the liquid phase prior to heating the gaseous phase. In a closed container, the temperature and the pressure will rise until the supercritical state is reached. Water exhibits a heat capacity of 1 cal per gram per degree Kelvin at room temperature. Once it reaches the supercritical state, water exhibits a heat capacity that goes to infinity. Thus, by employing the present invention, it is possible to apply enough energy to effect the conversion of liquid water into supercritical water and to maintain it at that state while providing a given level of microwave energy. The resulting supercritical water can be used in other applications, as is the case for supercritical water generated by other technologies. While water is used only as an example, it will be understood that the invention is not limited to water as will be evident to those skilled in the art.

In one preferred configuration of the present invention, an apparatus is provided so that such a membrane is allowed to establish a tight seal in the container enclosing the matrix of interest. The microwave power is applied and as the volatiles generation is effected, the membrane may be moved down toward the matrix so as to reduce the headspace volume above the matrix and the membrane. The semi-permeability of the membrane effects separation as the volatiles are not able to return to the liquid or solid phase. The rate of heating will allow for headspace type of experiments, or if disruption of the equilibrium is effected by applying extra power, then the method will lead to the generation of purge and trap-like experiments. The membrane can also be retracted to its original position thus compressing the volatiles into a smaller volume.

The apparatus, as generally set forth in FIG. 1, is particularly well-suited for interfacing directly onto the injector port, or other appropriate inlet mechanisms, of an appropriately selected analytical instrument, such as a gas, liquid or supercritical fluid chromatographic instrument. Such an arrangement, by opening of an appropriate valve, allows for on-line transfer of the gaseous volatile materials whereby one can effect a totally automated analytical protocol for headspace or purge and trap types of analysis with a single instrument, an option not available with any other current technology. The separation methods mentioned above were noted only for example purposes and it will be understood that they are not exhaustive nor limiting with respect to other applications of the process and apparatus, to other methods.

The sample used was water contaminated with west Texas sour crude oil at a concentration of 5 parts per million. Headspace analysis carried after a 30-minute incubation period at 358° K. while the analysis of the volatiles produced by the methodology of the invention was performed after a 30-second irradiation period. All analytical procedures were identical.

FIG. 1 illustrates one form of one aspect of the apparatus. As the volatiles are generated, a mobile semi-permeable or selectively membrane 18 disposed within container 10, moves in response to increasing gaseous pressure and then separates the newly generated gas phase from the liquid or solid phase matrix beneath the membrane 18, generally illustrated in dashed lines. Volatiles passing through membrane 18 exit the container 10 via conduit 20. Volatiles travelling through conduit 20 may be sampled by opening valve 22 for discharge through sampling line 24. The volatiles may additionally be forwarded to analysis means 26, which may comprise any known analysis apparatus, e.g. a gas chromatograph, I.R. spectrophotometer, N.M.R. apparatus, mass spectrometers, U.V. analysis means, etc.

Figure 3:
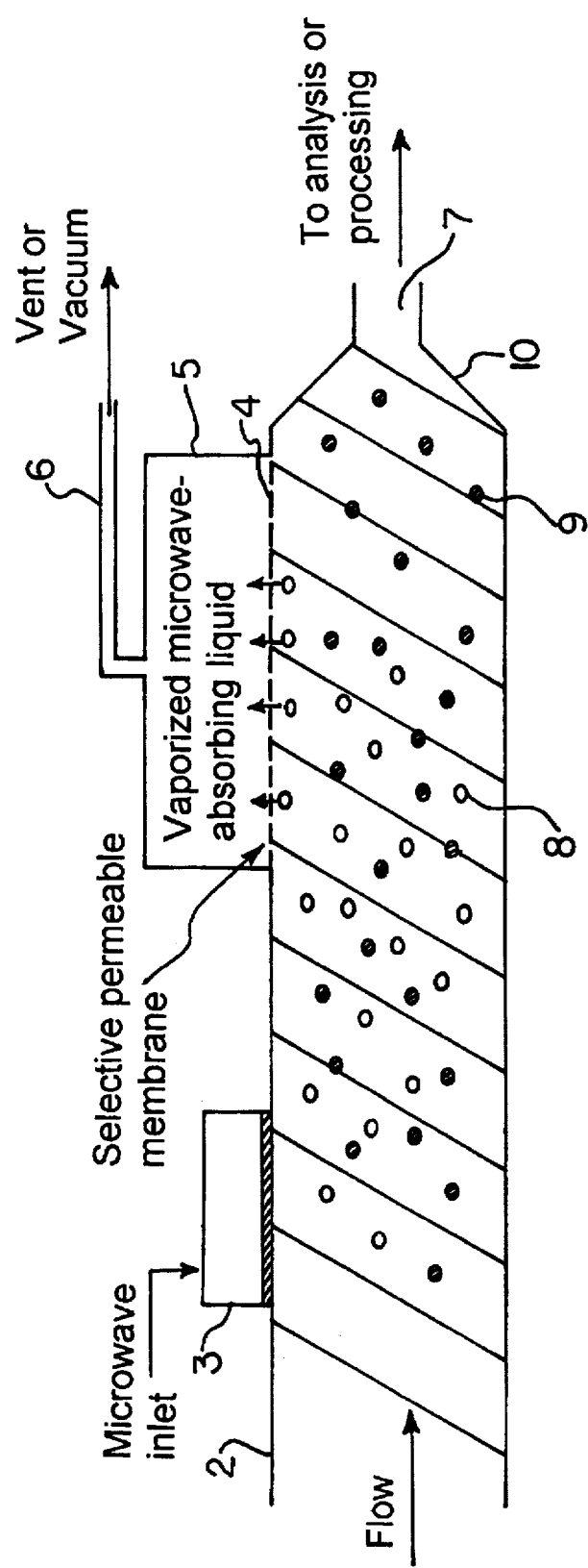
FIG. 3 is a diagram of a flow-through apparatus to separate a microwave-absorbing liquid as vapor from a matrix before analysis or further processing.

FIG. 3 illustrates one form of an apparatus for the removal of microwave-absorbing liquid from a matrix. A flow of liquid or solid matrix proceeds through conduit 2 past microwave inlet 3 where the matrix is exposed to microwave radiation selected to volatilize at least one microwave-absorbing component (shown as vapor pocket or bubble 8). These bubbles flow against or migrate to selective permeable membrane 4, pass through the selective membrane into enclosure 5 which may be vented or subject to a vacuum through line 6. The flow rate past the membrane can be slow enough to allow substantially complete separation of the volatiles: this slow flow rate is enhanced by constriction 10 before residual matrix exits at 7. In FIG. 3 one alternative is shown at 9 where a second liquid is volatilized by the microwave radiation but does not exit through membrane 4 and continues through exit 7 as pockets or bubbles 9 for subsequent separation e.g. as analyte.

Figure 4:
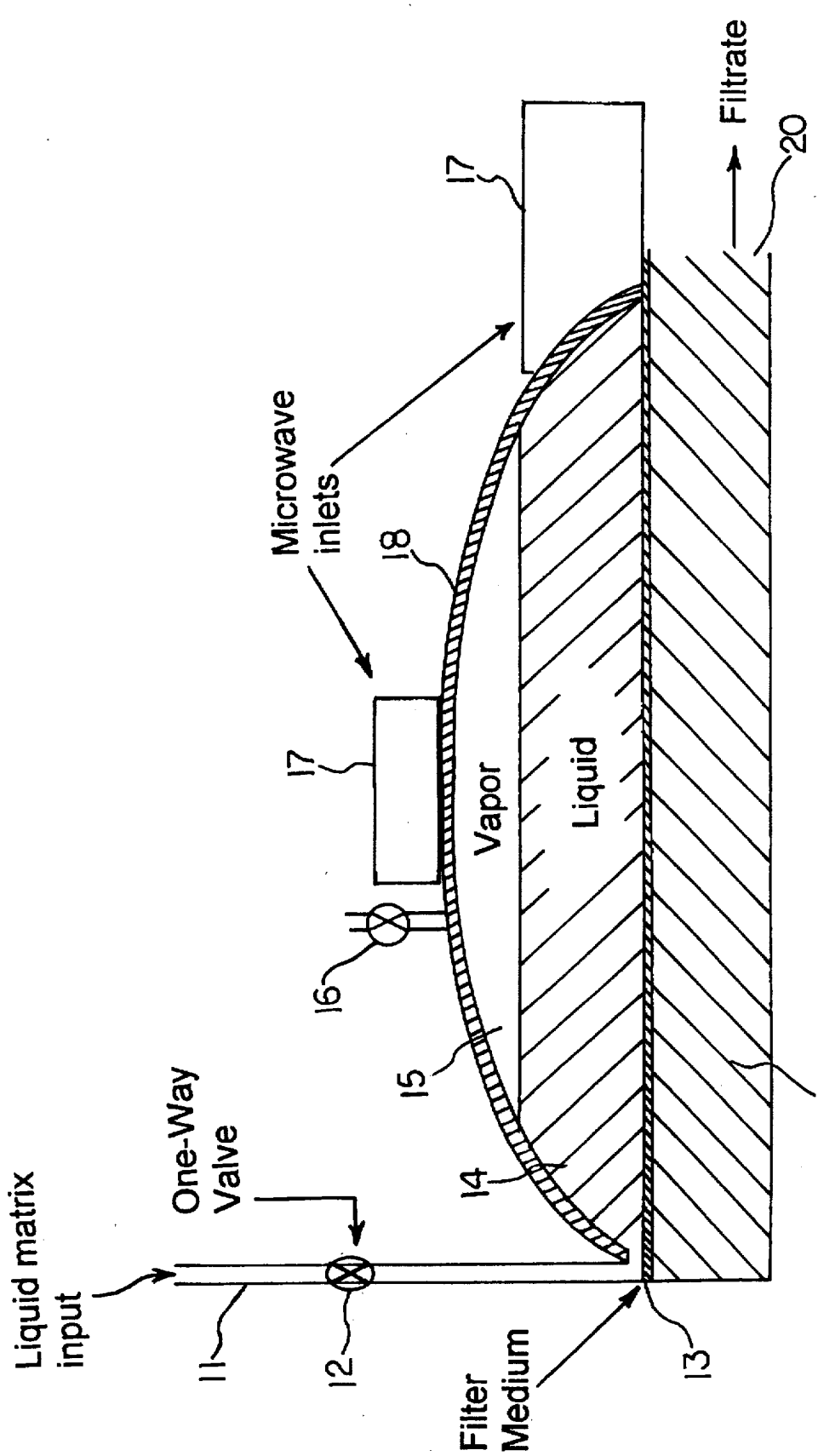
FIG. 4 is a diagram of a flow-through apparatus to utilize in situ microwave-generated vapor to pressurize liquid at the surface of a separation medium and increase flow rate through the medium.

FIG. 4 illustrates one form of an apparatus for separation (e.g. filtration) of a liquid suspension or liquid mixture. The liquid matrix enters through conduit 11 and one-way valve 12. The matrix enters vessel 18 near separation (e.g. filter) medium 13 and forms a liquid reservoir 14 against medium 13. Microwave radiation inlets are shown at 17 and are sited to direct selected radiation into liquid reservoir 14 to cause vaporization of microwave-absorbing liquid. The microwave-generated vapor is shown at 15 and exerts pressure against liquid 14 and thus against separation medium 13 and one-way valve 12. This in situ microwave-induced pressure is effective to increase flow of matrix through medium 13 into collector 19 and hence to exit 20. A vent 16 is shown to facilitate control of pressure. In a preferred mode, the pressure is allowed to increase until most of the liquid in reservoir 14 passes through medium 13, and then pressure released through vent 16. Fresh matrix then is introduced through conduit 11 and valve 12 and the cycle repeated.

In the embodiment shown in FIG. 3, the conduit 2 may take the form of a pipe or tube, or have a square, rectangular or other non-circular cross-section. The membrane 4 may form an upper portion (arc) or the complete circumference (annular) of a section of the pipe or tube configuration. In the latter case, the liquid matrix may be caused to swirl in the membrane region to increase exposure of pockets or bubbles 8 to the membrane. In the case of non-circular cross-section conduits 2, the membrane usually will take the form of a band across an upper surface downstream of the microwave inlet 3, this inlet 3 being substantially coextensive with the membrane band. The enclosure 5 will take the appropriate form to cover membrane 4.

In the embodiment in FIG. 4, conduit 11 may enter vessel 18 at any location, preferably so as to release fresh liquid matrix close to the surface of separation medium 13. In this pressure-enhanced separation embodiment, the vessel 18 may be configured as a rigid pipe and separation medium 13 as an annular concentric form within the pipe. Preferably separation medium 13 is supported against a rigid porous support (not shown). The vessel 18 (e.g. pipe) may be selected to be transparent to the microwave or the microwave inlets may be designed to access through appropriate regions. The liquid matrix will flow through the annular space between the pipe and medium and be subject to the microwave radiation. On vaporization of liquid, pressure will be generated in this annular space and will be directed by the rigid pipe against the separation medium to enhance flow through this medium. To prevent the pressure from being dissipated axially before the desired flow through the medium is achieved, it may be desirable to position valvest gates or constrictions to confine the pressure within the annular space surrounding the separation medium in the region where the microwave radiation is applied. Thus it is preferable to pass liquid matrix into this region intermittently and to cycle the microwave radiation/pressure appropriately. After separation the treated matrix or filtrate will exit at one or both ends of the medium annulus. The separation medium can be any solids-retaining medium, or any liquid- or solute-selective membrane. Various filter media, liquid permselective membranes or reverse osmosis membranes may be used.

Examples of the invention are provided below wherein microwave radiation-induced volatile generation was used. Disruption of the equilibrium normally present between liquid or solid substances and their gaseous state as described demonstrate improvements in one or more aspects. These aspects include yield, sensitivity, number of volatiles, identity of volatiles, reduced time and production costs (reduced operational costs and reduced capital costs), reduced number of operations and reduced process-related hazards (to humans and to sample integrity), or a combination thereof, over the conventional headspace and purge and trap processes currently used. These examples are illustrative and typical, but are not to be considered exhaustive or limiting.

EXAMPLE 1

As a representative example of headspace analysis, the volatiles from a water sample contaminated with a crude oil were obtained from a conventional headspace sampler and from this invention. Water was contaminated with some west Texas sour crude oil at a concentration of 5 parts per million. Two 10 mL aliquots were transferred into two identical 20 mL vials that were sealed hermetically. The first vial was then subjected to a 30-minute incubation period at 358° K. on a conventional, commercially available, headspace sampler (Hewlett Packard 19395A). A 1-mL volume of the resulting headspace was injected directly into the injector port of a gas chromatograph (Hewlett Packard 5890 Series II, flame ionization detector) equipped with an appropriate column to effect the separation and the resolution of the volatiles (HP-1, 25 meters, 1 micrometer thickness).

The second vial was subjected to the process taught by this invention, namely by exposure to microwave radiation (2450 MHz, 650 Watts) for 30 seconds. A 1-mL volume of the resulting headspace was injected directly onto the injector port of a gas chromatograph under the same conditions as per the conventional headspace sampler.

Figure 2:
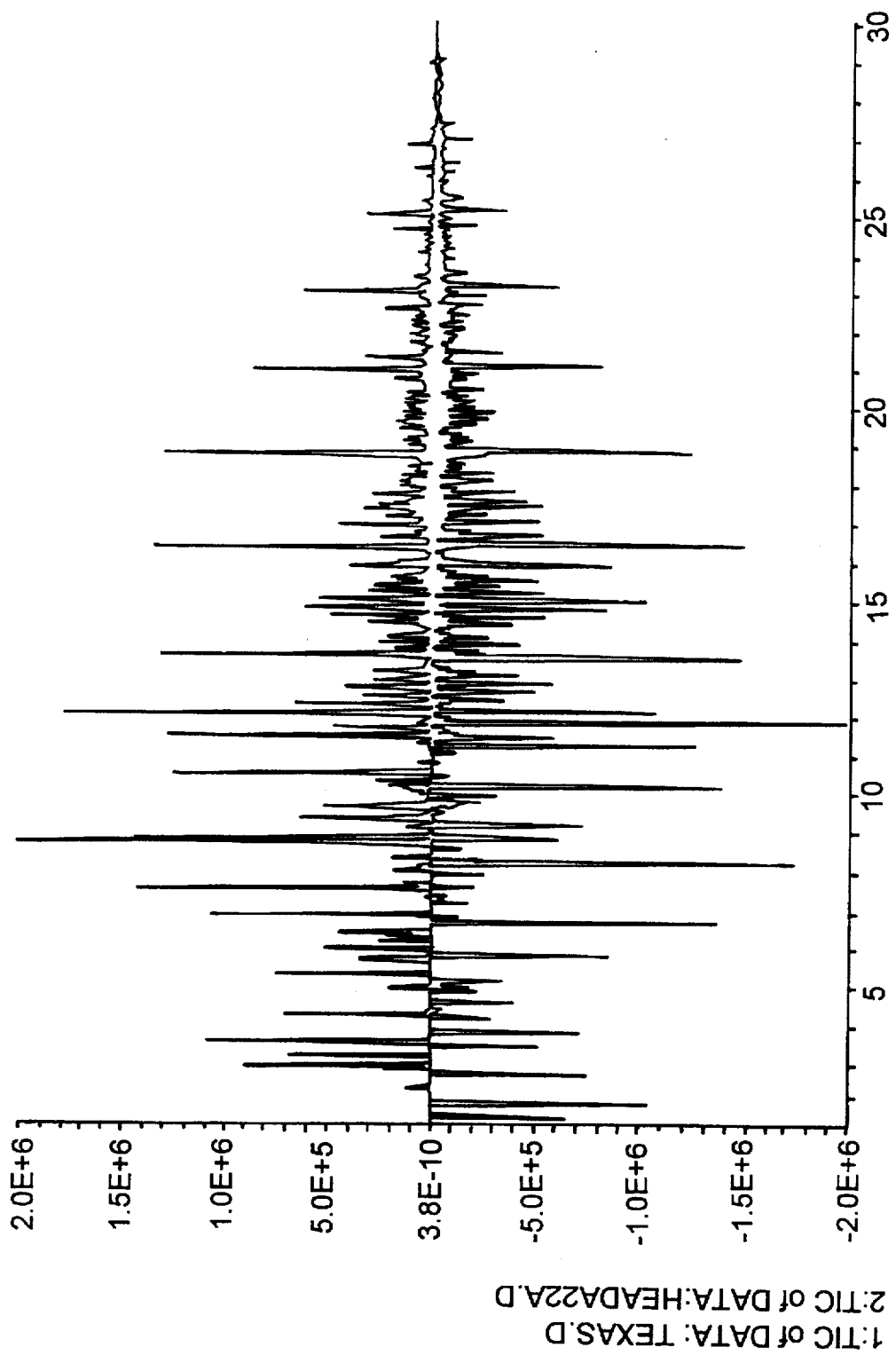
FIG. 2 is a comparison of the gas chromatograms of the volatiles obtained from conventional headspace analysis (top trace-labelled headspace) and from this invention (bottom, inverted trace-labelled MAP)

FIG. 2 shows the two resulting traces recorded under identical conditions, both scales being the same. This example demonstrates that the methodology of the present invention yielded more volatiles, in terms of their overall absolute quantity, in a much reduced sampling time. Furthermore, this example also shows that the use of this invention led to the detection of more components, principally for the more volatile substances, hence an evidence that the excess energy applied to the system was absorbed selectively by the liquid phase over the gaseous phase.

EXAMPLE 2

Fresh sage, of 80% moisture content, obtained from Saint-Jean-sur-Richelieu, Quebec, Canada, was chopped coarsely into pieces and subjected to conventional purge and trap analysis as well as to conventional headspace analysis.

A portion of the same material was inserted into a container. The container was sealed by a cover through which an orifice had been made. A commercially available sorbent, in an appropriate container, was fitted from the inside of the container to the orifice thus creating an hermetic seal. The container and its contents were then treated by exposure to microwave radiation for 90 seconds so as to severely disrupt the equilibrium that existed between the solid plant material and the gases around it. The sorbent was then eluted and the eluate analyzed by gas chromatography. The results of the analysis evidenced the presence of volatile terpenoids as well as less volatile ones.

A typical analysis contained 4-carene, alpha-thujene, alpha-pinene, camphene, 2-beta-pinene, sabinene, beta-myrcene, 1,8-cineole, beta-phellandrene, alpha-terpinolene, alpha-thujone, beta-thujone, camphor, bornyl acetate, cis-caryophyllene, and alpha-caryophyllene. This analysis compared favourably to the purge and trap analysis, while being superior to the headspace analysis, the latter lacking some of the lesser volatile compounds (sesquiterpenoids).

It will be evident to those skilled in the art that the choice of sorbent is dependent upon the nature of the volatiles of interest (in the present example, a silica sorbent was appropriate). Direct injection of the volatiles without the use of any trap of any kind (cold or sorbent) is possible by the use of this invention because of the short sampling duration and because of the relatively small volume of sampling necessary. Purge and trap would not allow such a direct injection without a cold trap of kind, or of a sorbent. The use of this invention, in this particular example, showed that a purge and trap analysis can be performed more rapidly, with less operations (hence reduced risks of sample loss or sample degradation), at a much reduced cost and with less energy than conventional technology. Again, the use of this invention requires less intricate equipment occupying a much reduced space and obtainable at a much reduced capital cost.

EXAMPLE 3

As a representative example of headspace analysis of a solid matrix, the volatiles from a soil sample contaminated with a crude oil were obtained from a conventional headspace sampler and from this invention. The soil was contaminated with west Texas sour crude oil at a concentration of 4.28 parts per million. Two 1.0 g aliquots were doped with 0.5 mL of water and were transferred into two identical 20 mL hermetically sealed vials. The first vial was subjected to a 30-minute incubation period at 358° K. on a conventional, commercially available, headspace sampler (Hewlett Packard 19395A). A 1-mL volume of the resulting headspace was injected directly into the injector port of a gas chromatograph (Hewlett Packard 5890 Series II, flame ionization detector) equipped with an appropriate column to effect separation and resolution of the volatiles (HP-1.25 meters, 1 micrometer thickness).

The second vial was subjected to the process according to the present invention, namely by exposure to microwave radiation at a frequency of and a power rating of 650 Watts for 30 seconds. A 1-mL volume of the resulting headspace was injected directly into the gas chromatograph under the same conditions as per the conventional headspace sampler.

The results obtained through this example demonstrate that the sample, when treated according to the present invention, yielded more volatiles, in terms of their overall absolute quantity, in a substantially reduced sampling time and that the nature of the volatiles is exactly identical to that obtained by conventional technology. Furthermore, this example also evidences that the excess energy applied to the system was absorbed selectively by the solid (and small amount of liquid) phase over the gaseous phase.

EXAMPLE 4

This example relates to headspace analysis in the biomedical and forensic fields and indicates usefulness in alcohol detection from an aqueous sample.

The detection of alcohol from an aqueous sample was performed on a conventional headspace sampler and by using the methodology of the present invention. Water was spiked with ethanol at a concentration varying between 0.8 to 80 mg per 100 mL. Two 10 mL aliquots were transferred into two identical 20 mL hermetically sealed vials. The first vial was then subjected to a 30-minute incubation period under conditions set forth in Example 3. A 1-mL volume of the resulting headspace was injected directly into the injector port of a gas chromatograph equipped with an appropriate column to effect the separation and the resolution of the volatiles, these apparatus being those indicated in Example 3. The second vial was subjected to the process taught by this invention, namely by exposure to microwave radiation (2450 MHz, 650 Watts) for 30 seconds. A 1-mL volume of the resulting headspace was injected into the injector port of a gas chromatograph under the same conditions as per the conventional headspace sampler. An identical experiment was performed by substituting whole cream (35% fat) to water, cream being a most challenging matrix with which to work. The results of this example demonstrate that this invention was more sensitive by a factor of at least 2, required a much reduced sampling time, and provided for the detection of more species (in the case of the cream).

The overall reduction in analysis time evidenced in this example is of extreme importance to forensic and biomedical applications such as the determination of the ethanol content in blood for drivers suspected to be under the influence of alcohol and for the monitoring of dissolved gases in blood of patients undergoing surgery. Again, the example also shows that the use of the invention allowed the excess energy applied to the system to be absorbed selectively by the liquid phase over the gaseous phase.

EXAMPLE 5

This example describes one gas-phase extraction method for the headspace analysis of volatile organic compounds, often referred to as VOCs, in water, and compares the results to those obtained by conventional static headspace analysis in terms of sensitivity, linearity, precision, and sample preparation time.

A 10-component purgeable aromatics standard solution (2.0 mg/mL of each component in methanol; components being benzene, toluene, ethylbenzene, chlorobenzene, o-, m-, and p-xylenes, and 1,2- 1,3 and 1,4-dichlorobenzenes, Hewlett-Packard Part No. 8500-6080, Method 8020) was diluted to 1, 4, 20, 100 and 500 ppm with methanol. A series of 10-mL water samples, contained into 20-mL headspace vials, were spiked at 10, 40, 200, 1000, and 5000 ppb of each component by adding 100-μL aliquots of the diluted solutions (Drummond fixed volumes micro-pipette). Blanks consisted of 10-mL water samples that were spiked with one 100-μL aliquot of methanol alone and they were used to monitor the potential interferences arising from the solvent. All samples were capped within five minutes form the end of the spiking procedure and were left to stand for at least 24 hours before the experiments were performed.

A microwave oven was used to apply the microwave energy to the samples for microwave treatment (microwave assisted process, MAP™) gas-phase extraction experiments. The power level was kept low to minimize the over-pressurizing of the headspace vials and the potential for losses due to leaks or the potential for explosion. A wide range of experimental conditions were investigated. The results reported in this example were obtained under the following conditions: Extraction: Microwave power 500 W; Frequency 2450 MHz; Irradiation and spinning cycle of 15 s irradiation, 5 s of spinning, 15 s of irradiation and 5 s of spinning (total sample preparation time of 40 s); Sampling: Sampling was effected by using a headspace sampler (Hewlett-Packard 7694) operated with a loop temperature of 90° C.; Transfer line temperature of 100° C.; Vial pressurization time of 0.2 min.; Loop fill time of 0.2 min.; Loop equilibration time of 0.05 min.; and sample injection time of 0.4 min. (equilibration time of 0 min.). The headspace sampler was fitted with a 0.5 m heated transfer line. All experiments were performed several times and triplicates were run at each occasion.

The resulting headspace was analyzed using a Hewlett-Packard gas chromatograph 5890, Series II Plus, equipped with a split-splitless SS inlet and a flame ionization detector. An HP-5, 30 m×0.32 mm i.d. fused silica column capillary column with a film thickness of 1.0 μm, was used. Operating conditions were as follows: Inlet temperature 250° C.; Detector temperature 250° C.; Temperature program 60° C. for 0.5 min., 60° C. to 120° C. @10° C./min., held at 120° C. for 3.5 min (total run time of 10 min.); Helium carrier gas at 2 mL/min.; constant flow mode (8 psi at 60° C.); Sample loop of 1.0 mL, split flow of 20 mL/min. (1:10 split ratio); Headspace vial pressurization maintained at 22 psi via the channel D of the HP 5890 electronic pressure control unit.

For comparison purposes, static headspace sampling experiments were performed using the same headspace sampler. Optimized operating conditions for the matrix of interest were as follows: Extraction: Oven temperature at 80° C.; Vial equilibration time of 30 min.; Agitation at maximum (setting 2); Sampling and gas chromatographic analysis: Exactly as per the microwave gas-phase experiment above. All experiments were also performed several times and triplicates were run at each occasion.

Tables 1 and 2 provide precise information about the sensitivity, the linearity, and the reproducibility data obtained from both methods. Both methods were characterized by regression coefficients greater than 0.9999. The analytes sensitivity, however, was significantly better for MAP gas-phase extraction with response signals greater by circa 35% for each component at each concentration. The relative standard deviation, that included the total systemic error factor, was also better for the Microwave Treatment with an overall value of 1.4% (between 0.19% and 2.3%) whereas that of conventional static headspace was at 2.3% (between 1.3% and 3.3%).

The greater sensitivities obtained are the result of the microwave energy being imparted more selectively to the water because the latter absorbs microwaves preferentially to the surrounding gaseous medium. This energy is then released to the neighbouring low-absorption species (volatile organic compounds, VOCs) which are, in turn, vaporized selectively and rapidly in proportions that are related to their vapor pressure and to their heat capacity.

TABLE 1

Linearity data (from gas chromatography-flame ionization detector results) for 30-minute conventional status headspace and 40-second Microwave Treatment gas-phase extractions of volatile organic compounds (VOCs) in water

| Regression Data | Headspace | Microwave Treatment |
|---|---|---|
| Multiple R | 0.99999 | 0.99999 |
| R Square | 0.99998 | 0.99999 |
| Adjusted R Square | 0.99997 | 0.99999 |
| Standard Error | 9336 | 7390 |

TABLE 2

Comparative sensitivity and reproducibility data (from gas chromatography-flame ionization detector results) for conventional 30-minute static headspace sampling and 30-second Microwave Treatment gas-phase extraction of volatile organic compounds (VOCs) from water

| Concen- | Headspace | | Microwave Treatment | | Microwave Treatment/ Headspace |
|---|---|---|---|---|---|
| tration | Response | RSD* | Response | RSD* | Ratio |
| 10 ppb | 9830 | 3.30 | 12860 | 2.18 | 1.31 |
| 40 ppb | 35600 | 3.21 | 47869 | 2.30 | 1.34 |
| 200 ppb | 178100 | 1.62 | 241021 | 1.50 | 1.35 |
| 1,000 ppb | 853516 | 2.11 | 1194101 | 0.19 | 1.40 |
| 5,000 ppb | 4348711 | 1.29 | 5892204 | 0.79 | 1.35 |

*Relative Standard Deviation

Microwave Treatment gas-phase extractions make use of physical phenomena, that are fundamentally different from those applied in conventional sample preparation techniques. It provides for dramatic reduction in the preparation time required per sample—here from 1800 to 40 seconds, a factor of 45. In addition, in the analytical example presented herein, microwave treatment gas-phase extraction also offers significant advantages over static headspace in terms of sensitivity, while offering better reproducibility and similar characteristics. It will be evident to those skilled in the art that the dramatic reduction in sample preparation time, on a per sample basis, along with the relative ease of rapidly implementing widely varying operating parameters are attributes of choice for methods to be used during field analytical activities.

EXAMPLE 6

This example describes one microwave treatment gas-phase extraction method for the headspace analysis of volatile organic compounds, often referred to as VOCs, in soils, and compares the results to those obtained by conventional static headspace analysis in terms of sensitivity, linearity, precision, and sample preparation time.

A 7-component purgeable aromatics standard solution (components being benzene, toluene, ethylbenzene, chlorobenzene, and 1,2-, 1,3 and 1,4-dichlorobenzenes) in methanol was used to spike 1-gram natural agricultural soil samples contained into 20-mL headspace vials at 1, 10, 0.25, 0.50, 1.00, 2.50 and 5.00 ppm. Blanks consisted of 1-gram natural agricultural soil samples that were spiked with an aliquot of methanol alone and used to monitor the potential interferences arising from the solvent. All samples were capped within five minutes from the end of the spiking procedure and were left to stand for at least 24 hours before the experiments were performed.

A microwave oven was used to apply microwave energy to the samples for microwave treatment gas-phase extraction experiments. The power level was kept low to minimize the over-pressurizing the headspace vials and the potential for losses due to leaks or the potential for explosion. A wide range of experimental conditions were investigated. The results reported in this example were obtained under the following conditions:

Extraction: De-capping of vial, addition of a 2-mL aliquot of water and recapping of the vial; Microwave power 500 W; Frequency 2450 MHz; Irradiation and spinning cycle of 20 s irradiation, 5 s of spinning, 20 s of irradiation and 5 s of spinning (total sample preparation time of 50 s); Sampling: Sampling was effected by using a headspace sampler (Hewlett-Packard 7694) operated with a loop temperature of 90° C.; Transfer line temperature of 100° C.; Vial pressurization time of 0.2 min.; Loop fill time of 0.2 min.; Loop equilibration time of 0.05 min.; and sample injection time of 0.4 min. (equilibration time of 0 min.). The headspace sampler was fitted with a 0.5 m heated transfer line. All experiments were performed several times and triplicates were run at each occasion.

The resulting headspace was analyzed using a Hewlett-Packard gas chromatograph 5890 Series II Plus, equipped with a split-splitless SS inlet and a flame ionization detector. An HP-5, 30 m×0.32 mm i.d. fused silica column capillary column with a film thickness of 1.0 µm, was used. Operating conditions were as follows: Inlet temperature 250° C.; Detector temperature 250° C.; Temperature program 60° C. for 0.5 min., 60° C. to 120° C. @ 10° C./min., held at 120° C. for 3.5 min. (total run time of 10 min.); Helium carrier gas at 2 mL/min.; constant flow mode (8 psi at 60° C.); Sample loop of 1.0 mL, split flow of 20 mL/min. (1:10 split ratio); Headspace vial pressurization maintained at 22 psi via the channel D of the HP 5890 electronic pressure control unit.

For comparison purposes, static headspace sampling experiments were performed using the same headspace sampler. Optimized operating conditions for the matrix of interest were as follows: Extraction: De-capping of vial, addition of 2-mL aliquot of water and recapping of the vial; Oven temperature at 80° C.; Via equilibration time of 30 min.; Agitation at maximum (setting 2); Sampling and gas chromatographic analysis: Exactly as per the microwave gas-phase experiment above. All experiments were also performed several times and triplicates were run at each occasion.

Both methods showed good linearity although the overall sensitivity was significantly better for microwave treatment gas-phase extraction than static headspace with response signals greater by circa 50%. Furthermore, the conventional headspace methodology was unable to yield quantitative results for samples spiked at 0.10 and 0.25 ppm as well as for some components in the 0.50 ppm samples; the microwave experiments on the other hand, were quantifiable from 0.25 ppm onwards.

As it will be clearly understood by those skilled in the art, the microwave absorbent material, due to the vaporization thereof may require replenishment. Where the absorbent material comprises, for example, water, the material may be hydrated prior to microwave exposure or may be rehydrated subsequent to treatment.

It will be appreciated by those skilled in the art that the process is applicable to systems which include a plurality of phases. An example of such a system can be seen in the expression of volatile materials from a capillary sampling tube. The extraction of volatilizable materials from conventional methods is not only extremely difficult using present technology, but further results in the potential for significant losses of the material to be extracted. By employing the microwave process according to the present invention, extraction or expression of the materials is substantially complete and results in a substantial reduction in volume losses of the material to be expressed.

EXAMPLE 7

This example is relevant to other currently used disposable analytical devices. This application of the invention is related to the extraction from natural or synthetic fibres, e.g. hollow fibres used in so-called solid-phase micro-extraction applications of compounds, e.g. contaminants, such as, volatile organics from aqueous solutions. Such fibrous materials are often used as a means to concentrate analytes prior to releasing them into an inlet of an analytical apparatus, e.g. by desorbing them into the inlet of a gas chromatograph.

There is a need to release chemicals from the fibres as rapidly as possible. To demonstrate the advantages associated with the use of the present invention, commercially available hollow fibres were used in so-called solid-phase micro-extraction Supelco. All the fibres were preconditioned in the manner prescribed by the manufacturer until the fibres proved to be fee of contaminants. The fibres were then used as prescribed by the manufacturer to effectively sample and concentrate the contaminants. In this example, BTEX (i.e. benzene, ethylbenzene, toluene, xylenes) were the contaminants found in a water sample. Water aliquots of similar volumes were used and the sampling time (i.e. immersion of fibre into the water sample) was kept constant, for all experiments (15 minutes).

Once the sampling time had elapsed, the fibres were cut from their holders and put into series of two hermetically-sealed 20-mL headspace analysis vials. The first vial of the series was then subjected to exposure to heat in a conventional oven at 353° K. for a 30-minute period. A one-mL volume of the resulting headspace was injected manually at 498° K. over a 45 second period into the splitless inlet port Of a gas chromatograph (HP-5890 Series II), appropriately fitted with a flame ionization detector (at 553° K.) and a SPB-1 column (30 m, 0.53 mm i.d., 1.5 µm film thickness). The second vial was treated with a single 15-second, 900-watts, 2450 MHz microwave-irradiation period. A one-mL volume of the resulting headspace was analyzed in a similar manner as the first vial.

The conventional heating experiments failed to produce any recordable traces of the contaminants, whereas the microwave-treated samples led to recognizable patterns. To further demonstrate the advantages of this invention, more experiments were carried out with other types of sealed container, e.g. 3-mL disposable syringes properly fitted with a 24-gauge needle sealed with a teflon disc, 2-mL and 4-mL sample vials, etc. The results of these experiments led to the conclusion that the volume of the container is an important parameter in the sensitivity of the method.

It will be evident to those skilled in the art, that the use of the teachings of the present invention with an appropriately designed container, such container being, e.g. an inlet of a given analytical instrument, e.g. gas chromatograph, properly fitted with a microwave source, leads to much faster gas-phase extraction of contaminants from the fibres, thus removing the potential need for focusing techniques. Furthermore, it will also be evident to those skilled in the art that the use of this invention applies to samples that were collected from the liquid phase as well as from the gaseous phase of a solution contained into a vial, or collected directly from a gas, or a gaseous solution, or a gas mixture, be it enclosed or not (e.g. air sampling).

Similar work with difficult to analyze samples, such as potting soils (40 second total preparation time here) were performed and led to similar conclusions, namely that the use of this technology allowed for the quantitation of analytes at much lower levels than is possible with current static headspace technologies. Here again, microwave treatment gas-phase extractions make use of physical phenomena that are fundamentally different from those applied in conventional sample preparation techniques. In these particular examples it also provides for a dramatic reduction in the preparation time required per sample —from 1800 to 40–50 seconds, a factor of 36–45. It will be evident to those skilled in the art that the dramatic reduction in sample preparation time, on a per sample basis, along with the relative ease of rapidly implementing widely varying operating parameters are attributes of choice for methods to be used during field analytical activities. Hence, e.g. coupled to a total organic vapor analyzer, this invention provides for unequalled sensitivity performance. The latter attribute is of particular importance in applications where the safety of workers or that of the general public is involved such as is the case during controlled decontamination work, or during emergency response situations, respectively.

In the flow-through separations the selectivity of the membrane or filter medium can be chosen to allow the passage of the desired components—as provided for in previous examples—or to allow the passage of the medium used to dissolve the materials, or, as it will be evident to those skilled in the art, to remove the solvent. Preferred embodiments of this invention include, but are not limited to, enhancement of aqueous solution filtration processes, concentration of volatile organic compounds from water for interfacing to gas chromatographic analysis, concentration of organic substances for interfacing to liquid chromatographic analysis, and as a process to be used with appropriate equipment to remove solvents from solutions—in particular water—prior to the introduction of the resulting analytes into a detector means such as an infrared device or a mass detection device such as a mass selective detector, a mass spectrometer, a light scattering detector or the like, often used in e.g. liquid chromatographic systems.

In the case of solvent removal as liquid e.g. water for example, the rate of filtering will be greatly enhanced when submitted to the benefit of this invention as a result of the increase in pressure created by the application of microwaves to the aqueous solutions. Furthermore, in current use it is necessary to rinse the filter with significant volumes to ensure that all aliquots of the solution have been subjected to the filtration process. The use of this invention, combined with a judicious selection of a permeable membrane, will minimize significantly the need to rinse and reduce the possibility of tainting results due to added contaminants or introduced sources of interference.

In another embodiment of this invention, the permeable membrane is selected so as to allow the selective passage of the solvent in a dynamic mode as vapor. In one particular example, an aqueous solution is allowed to flow through a physical cavity that is equipped with a selective membrane and with means to subject the solution, while in the cavity, to microwave energy. The solution is allowed to flow in the cavity while being exposed to microwaves so as to effect the selective heating of the water until the water volatilises at which time it can escape through the membrane while the other constituents continue their movement through the chamber and reach an outlet at which point they exit as an enriched solution or as a mixture of substances devoid of water. It will be obvious to those skilled in the art that the presence or not of water in the material exiting the cavity can easily be controlled by applying the required amount of energy to effect partial or total volatilisation (can be calculated from the knowledge of the flow rate and the dead volume of the cavity). The use of this invention will be of particular interest for applications where it is necessary to concentrate the contents of analytes which are present in low quantities, even in ultra-tracequantities during e.g. liquid chromatographic analyses.

It will be obvious to those skilled in the art that this preferred embodiment applies especially well to, although is not limited to, its implementation within processes involving chromatographic techniques e.g. gas, liquid, or supercritical fluid chromatography, and detection techniques performed under vacuum conditions e.g. mass spectrometer or that require very low water residue to be effective e.g. Infrared detector.

It is possible to vaporize part or all of the liquid to be vaporized by adjusting the amount of energy delivered by the microwave generator. Knowing the amount of liquid to be vaporized, its heat capacity and boiling point, one can calculate the amount of energy to be delivered.

The separations can be carried out with a continual flow-through, or with continuous flow and intervals of minimal flow in which separation proceeds and conditions are adjusted, before another cycle. In the latter case, the microwave radiation may be interrupted or pulsed for optimum separations.

Although embodiments of the invention have been described above, it is not limited thereto and it will be apparent to those skilled in the art that numerous modifications form part of the present invention insofar as they do not depart from the spirit, nature and scope of the claimed and described invention.

I claim:

1. A method of improving flow-through separations from a matrix having a microwave-absorbing liquid component, comprising:
   exposing a flow of the matrix to microwave radiation treatment to vaporize microwave-absorbing liquid;
   processing the vapor in one of the following two ways:
   i) flowing the vapor through a permeable membrane selective therefor and removing the vapor; and
   ii) enclosing the vapor and matrix in a confined space in contact with a separation medium and flowing treated matrix through this separation medium to separate a component; and
   recovering the residual matrix.

2. The method of claim 1, wherein the matrix flow is intermittent in timed relation with intermittent microwave radiation.

3. The method of claim 1, wherein the permeable membrane or separation medium is in a form selected from planar and annular.

4. A method of rendering a solid or liquid matrix containing a microwave-absorbing liquid and a component to be analyzed or processed, more suitable for such analysis or processing, comprising:
   exposing the matrix to microwave energy to vaporize at least one microwave-absorbing liquid;
   passing a vaporized liquid through a selective permeable membrane to separate a vaporized component before the matrix is heated significantly;
   recovering the residual matrix and any residual vapor; and
   passing the residual matrix and any residual vapor to means selected from analysis means and processing means.

5. The method of claim 4, wherein water is present in the matrix as a preferentially-microwave-absorbing liquid, the water is preferentially vaporized by the microwave and the membrane is a selective water-vapor-permeable membrane.

6. The method of claim 4, wherein two separate liquids are vaporized, one passes through a selective permeable membrane and the other is separated in a later step.

7. A method of increasing the rate of filtration of a liquid matrix through a filter able to separate a non-microwave-absorbing component of the matrix, the matrix including a microwave-absorbing liquid comprising:
   exposing the liquid matrix to microwave radiation to vaporize the microwave-absorbing liquid in a confined space upstream of the filter thereby generating a pressure against the filter surface; and
   maintaining the pressure by continued microwave radiation exposure while passing the matrix through the filter to generate a filtrate.

8. The method of claim 7, wherein the matrix is a liquid suspension of solids and the filter is a solids-retaining medium.

9. The method of claim 7, wherein the matrix is a liquid-liquid mixture and the filter is a liquid-selective membrane.

10. The method of claim 7, wherein the matrix is a liquid solution and the filter is a reverse osmosis membrane.

11. The method of claim 7, wherein the microwave radiation, pressure build-up and filtration proceeds in cycles.

* * * * *